United States Patent
Song

(10) Patent No.: US 11,285,008 B1
(45) Date of Patent: Mar. 29, 2022

(54) HIP IMPLANT WITH COMPRESSION RESISTANCE AND SELF-CENTERING FEATURES

(71) Applicant: Omnes Medical Inc., Houston, TX (US)

(72) Inventor: Benjamin Sooil Song, Los Angeles, CA (US)

(73) Assignee: Omnes Medical Inc., Houston, TX (US)

(*) Notice: Subject to any disclaimer, the term of this patent is extended or adjusted under 35 U.S.C. 154(b) by 0 days.

(21) Appl. No.: 17/091,341

(22) Filed: Nov. 6, 2020

Related U.S. Application Data

(60) Provisional application No. 62/932,842, filed on Nov. 8, 2019.

(51) Int. Cl.
*A61F 2/32* (2006.01)
*A61F 2/36* (2006.01)
(Continued)

(52) U.S. Cl.
CPC .............. *A61F 2/3662* (2013.01); *A61F 2/34* (2013.01); *A61F 2/3601* (2013.01);
(Continued)

(58) Field of Classification Search
CPC ........ A61F 2/34; A61F 2/4609; A61F 2/3662; A61F 2/3609; A61F 2/3859; A61F 2/32;
(Continued)

(56) References Cited

U.S. PATENT DOCUMENTS 4,608,055 A * 8/1986 Morrey ..................... A61F 2/36
                 623/22.46
5,591,233 A * 1/1997 Kelman .............. A61F 2/30965
                 606/76

(Continued)

OTHER PUBLICATIONS

K. Issa et al., "Osteonecrosis of the femoral head", The Bone & Joint Journal, Bone Joint J 2013; 95-B, Supple A:46-50, 5 pages.

(Continued)

*Primary Examiner* — Ann Schillinger
(74) *Attorney, Agent, or Firm* — Mark Protsik; Thomas Schneck

(57) ABSTRACT

A hip implant comprises an acetabular cup to be inserted into an acetabulum of a pelvis, together with a femoral head and neck portion and a main body shaft to be inserted into the femoral neck and proximal femoral shaft. The femoral head and acetabular cup form a smooth spherical-surface joint. The femoral head on a femoral head base is attached to a femoral neck rod, which has a tapered end that engages in a hole through the main body shaft, i.e. the main body shaft has a diagonal hole therethrough located at the center line of the neck of the femur to receive the tapered end at a specified angle that aligns with center line of the neck. A secured lock mechanism, insertable into the main body shaft above the diagonal hole, can be screwed down to compressively engage the tapered end of the femoral neck rod. The diagonal hole (and matching tapered end of the femoral neck) can have an overlapping two-circle cross-section, can have a specified taper angle, and a choice of incline to match a patient's femoral angle between the neck and shaft. The tapered neck rod can have wedge-shaped locking surface features to provide even more stability.

6 Claims, 12 Drawing Sheets

(51) Int. Cl.
| | | |
|---|---|---|
| *A61F 2/30* | (2006.01) | |
| *A61F 2/46* | (2006.01) | |
| *A61B 17/72* | (2006.01) | |
| *A61B 17/74* | (2006.01) | |
| *A61F 2/34* | (2006.01) | |

(52) U.S. Cl.
CPC ............ *A61F 2002/30433* (2013.01); *A61F 2002/30649* (2013.01); *A61F 2002/368* (2013.01); *A61F 2002/3652* (2013.01); *A61F 2310/00017* (2013.01); *A61F 2310/00023* (2013.01); *A61F 2310/00029* (2013.01); *A61F 2310/00059* (2013.01)

(58) Field of Classification Search
CPC ........ A61F 2/36; A61F 2/4607; A61F 2/4014; A61F 2/3601; A61F 2002/30433; A61F 2002/30649; A61F 2002/3652; A61F 2002/368; A61F 2310/00017; A61F 2310/00023; A61F 2310/00029; A61F 2310/0059
See application file for complete search history.

(56) References Cited

U.S. PATENT DOCUMENTS

| | | | | |
|---|---|---|---|---|
| 6,221,074 B1* | 4/2001 | Cole | ............ | A61B 17/72 606/60 |
| 6,319,286 B1* | 11/2001 | Fernandez | ............ | A61F 2/3609 623/23.18 |
| 8,579,985 B2* | 11/2013 | Podolsky | ............ | A61B 17/7283 623/22.42 |
| 8,668,695 B2* | 3/2014 | Schwammberger | ............ | A61B 17/7283 606/67 |
| 8,795,381 B2* | 8/2014 | Podolsky | ............ | A61F 2/32 623/22.11 |
| 8,840,675 B2* | 9/2014 | Song | ............ | A61F 2/36 623/22.11 |
| 9,433,449 B2* | 9/2016 | Vega | ............ | A61B 17/7266 |
| 2002/0133156 A1* | 9/2002 | Cole | ............ | A61B 17/744 606/62 |
| 2003/0074080 A1* | 4/2003 | Murray | ............ | A61F 2/4637 623/22.42 |
| 2003/0171819 A1* | 9/2003 | Sotereanos | ............ | A61B 17/744 623/22.42 |
| 2007/0050039 A1* | 3/2007 | Dietz | ............ | A61F 2/3609 623/19.13 |
| 2012/0143192 A1* | 6/2012 | Watanabe | ............ | A61B 17/7233 606/64 |
| 2015/0039093 A1* | 2/2015 | McTighe | ............ | A61F 2/4014 623/23.14 |
| 2015/0112345 A1* | 4/2015 | Boraiah | ............ | A61B 17/744 606/64 |

OTHER PUBLICATIONS

M. Scaglione et al., "Hip replacement in femoral head osteonecrosis: current concepts", Clinical cases in Mineral and Bone Metabolism 2015; 12(Suppl. 1):51-54, Supplemental to n.3 2015, 4 pages.

V.C. Bose et al., "Resurfacing arthroplasty of the hip for avascular necrosis of the femoral head", J Bone Joint Surg 2010;92-B:922-8, Oct. 8, 7 pages.

A.J. Wassef et al., "Use of an offset head center acetabular shell in difficult primary total hip arthroplasties", Annals of Translational Medicine 2019; 7(4):75, 7 pages.

\* cited by examiner

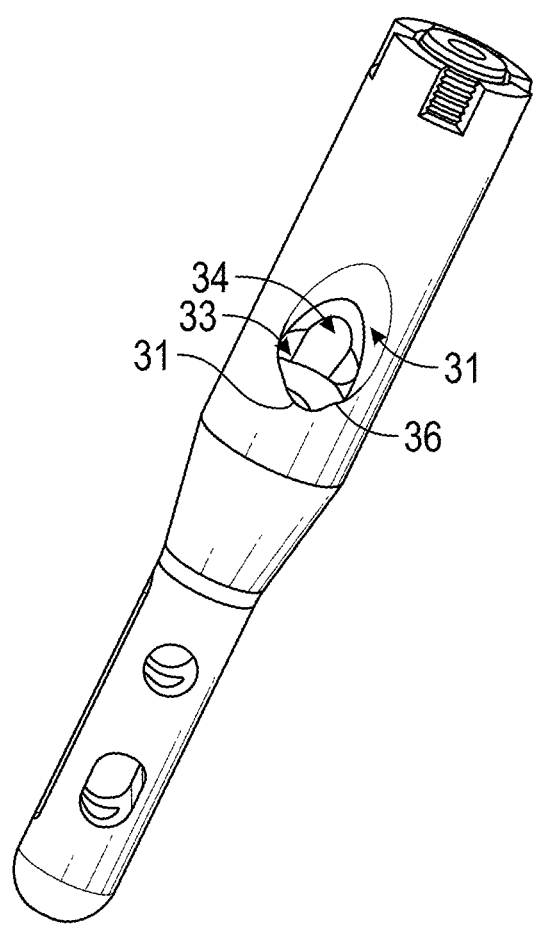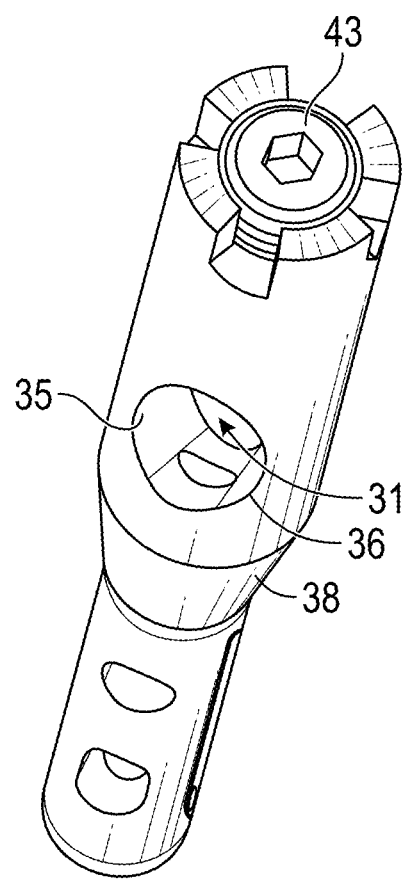
FIG. 11
FIG. 12

HIP IMPLANT WITH COMPRESSION RESISTANCE AND SELF-CENTERING FEATURES

CROSS-REFERENCE TO RELATED APPLICATION

The present application claims priority under 35 U.S.C. 119(e) from prior U.S. provisional application 62/932,842, filed Nov. 8, 2019.

TECHNICAL FIELD

The present invention relates to implants for total hip replacement and is especially adapted for use in patients that already have or are likely to develop osteonecrosis (also known as avascular necrosis) of the femoral head, with improved implant durability.

BACKGROUND ART

Hips form a ball-and-socket joint, where the ball is the femoral head at the upper end of the femur (thighbone) and the socket is formed by the acetabulum, which is part of the large pelvis bone. The surface of the ball and socket is covered with articular cartilage that enables them to glide easily across each other, allowing the joint to rotate. Osteonecrosis occurs when blood supply in a bone is disrupted due, for example, to traumatic bone or joint injury (dislocations and fractures), regular corticosteroid treatments, chronic elevated cortisone levels from alcoholism or obesity, and sickle cell or other disease conditions. Without adequate nourishment, osteocytes and related bone tissue die and the bone gradually degrades. This most commonly occurs to the femoral head in the hip joint. As the disease progresses, it becomes more difficult to stand and put weight on the affected hip and moving the hip joint is painful. The femoral head may eventually collapse completely, resulting in severe disability.

One possible treatment in severe osteonecrosis cases, is total hip replacement (THR). Studies of cumulative implant survival rates reveal that THR success has improved from just 47-63% after 4 to 5 years for first-generation prosthetic designs to about 93-96% after 8 to 10 years for current designs. However, osteonecrosis may affect the endurance of an implant, especially if it continues to progress into the femoral neck region. The ability of a hip implant to bear a load is normally assisted in part by the remaining femoral bone material, so any progressive degradation of the upper femur can lead in some circumstances to failure of the implant, for example by slippage of the femoral neck rod through its joint with the main implant shaft or a sudden change in the joint angle or even bending of the neck rod. Addition of bone cement to better secure the implant parts to the remaining bone material has improved outcomes, preventing or delaying, but not eliminating, failure of the prosthesis and the need for an eventual implant replacement. Many THR patients are still relatively young (under 40) and wish to maintain an active lifestyle, so even a small failure rate of 5% is deemed to be problematic. Thus, there is a need for further hip implant design improvements to further reduce, and preferably prevent, such failures.

FIGS. 1A and 1B show the femur angle 15, which is the angle between the line 14 which is passed through the center of distal femur 10 and trochanteric fossa 16 and the line 11 which is perpendicular to impinging line 13 and passed through the femoral neck mid-point 17. Impinging points 19 are identified with the connection of femoral circle 12 and femoral neck 18. Impinging line 13 is the line which connects two impinging points. For normal hips, the femur angle 15 is in a range of 136°±4°.

FIG. 2 shows how body weight force F transitions through the hip joint. This force from the body weight F may cause osteonecrosis, as shown in FIG. 3B, which crushes the femoral head and can cause hip implant failure. By way of comparison, a healthy hip is shown in FIG. 3A. Returning to FIG. 2, the reaction to the body weight force F consists of two force vectors. A first force vector f1 or bending force is resisted by both the implant's structure and remaining cortical bone. A second force vector f2 or axial force is the main force that may aggravate ongoing osteonecrosis in the remaining bone tissue. The implant's structure must be able to resist this force to relieve compressive stress upon the femoral neck and upper femur.

In a resurfacing hip implant, most of the cortical bone will be removed and only cancellous bone is there to hold the implant from pushing inside. This may not be enough to prevent the axial force from causing implant failure, as shown in FIG. 4. Prior gamma nail designs failed to protect from implant failure caused by the axial force.

SUMMARY DISCLOSURE

A hip implant is provided with an acetabular cup configured to be inserted into an acetabulum anatomy of a pelvis, together with a femoral head and neck portion and a main body shaft to be inserted into the femoral neck and proximal femoral shaft. The implant's replacement femoral head is on a femoral head base that is attached to a femoral neck rod and is configured to interface with the acetabular cup as a smooth spherical-surface joint. A feature of the present invention is that the femoral neck rod has a tapered end that engages in a hole through the main body shaft. That is, the main body shaft has a diagonal hole therethrough located at the center line of the neck of the femur to receive the tapered end of the femoral neck rod at a specified angle that aligns with the center line of the neck. A secured lock mechanism in the form of a compression screw set is insertable into the main body shaft above the diagonal hole and can be screwed down to compressively engage the tapered end of the femoral neck rod. The diagonal hole (and matching tapered end of the femoral neck rod) can have an overlapping two-circle cross-section, can have a specified taper angle, and a choice of incline to match a patient's femoral angle between the neck and shaft. In one embodiment, the tapered neck rod can have wedge-shaped locking surface features to provide even more stability.

BRIEF DESCRIPTION OF THE DRAWINGS

FIGS. 11 and 12 are two perspective views of a main body shaft of the implant showing upper and lower contact surfaces in the shaft's angled hole.

DETAILED DESCRIPTION

The hip implant of the present invention is designed to address potential implant failures that could be caused because of osteonecrosis. It does this by using a tapered lag screw in the implant structure to both resist movement of the femoral head and neck portions of the implant into the implant's main body shaft due to compression forces, and also resist bending failure of the implant with a more secure joint between the implant's tapered neck end and the stem of the main body shaft.

As is true of any implant to be inserted into (and remain in) the human body, the implant will be composed of sterile, bio-compatible materials that can endure the loads and stresses without substantial damage or failure for at least ten years. By way of example, strong bio-compatible metals may comprise any of cobalt, chromium, titanium, alloys thereof and medical-grade stainless steel 316. Suitable wear-resistant and bio-compatible (not biodegradable) polymers may comprise, for example, any of polyethylene, polyether ether ketone (PEEK), and ultra-high-molecular-weight polyethylene (UHMWPE). Implants in accord with the present invention will have an acetabular cup, femoral neck rod, compression screw set and main body shaft composed of a bio-compatible metal and will also have femoral head composed of a durable bio-compatible polymer.

Figure 1A:
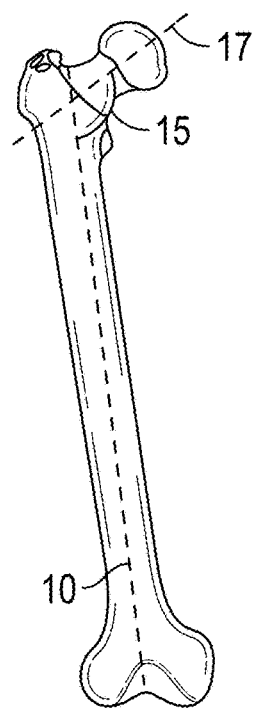
FIGS. 1A and 1B are respectively a side view of a femur and a close-up of the proximal femur, femoral neck and head, together with corresponding determinations of anatomical dimensions and angles.
Figure 1B:
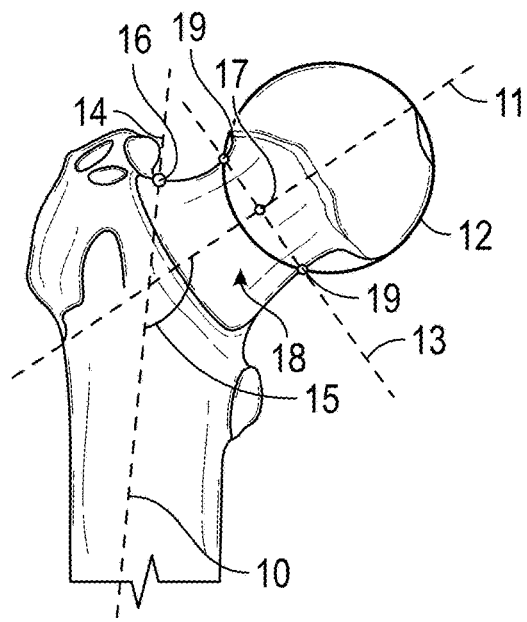
Figure 2:
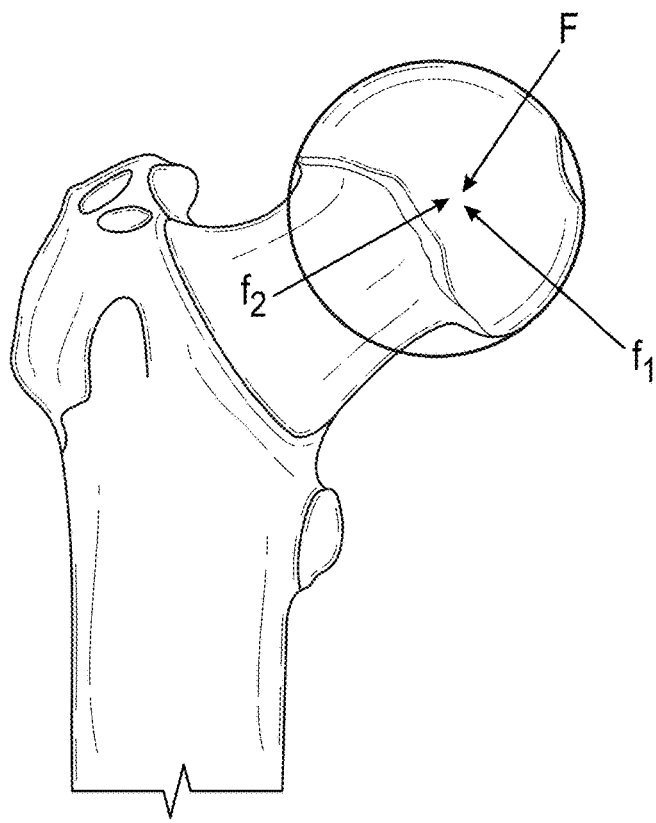
FIG. 2 is a close-up coronal view of a femoral neck and head, illustrating how body weight force transitions through the hip joint.
Figure 3A:
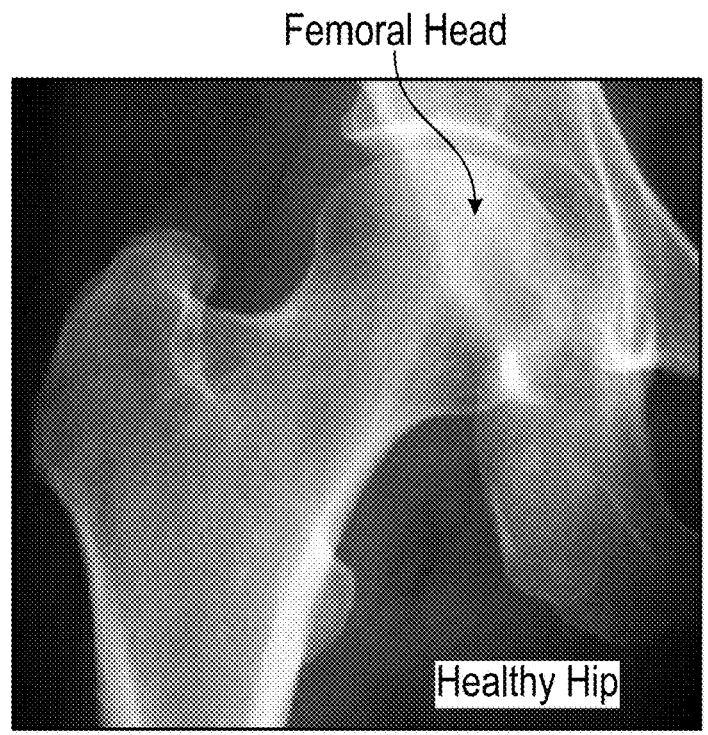
FIGS. 3A and 3B are coronal images of, respectively, a healthy hip joint and another hip joint with osteonecrosis.
Figure 3B:
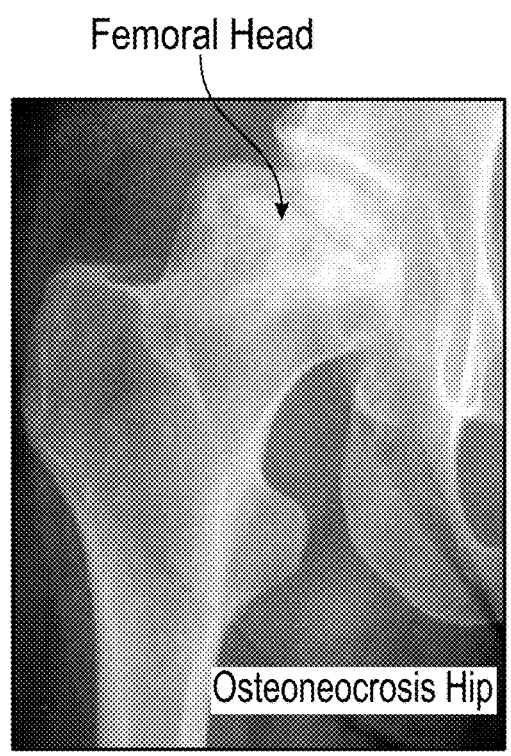
Figure 4:
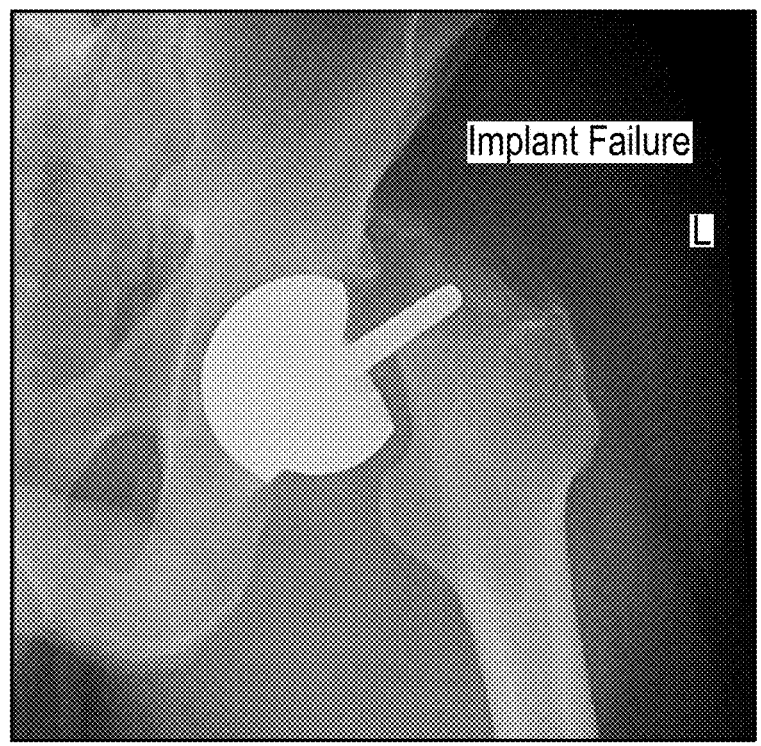
FIG. 4 is an image of a hip joint with an implant that has failed.
Figure 5:
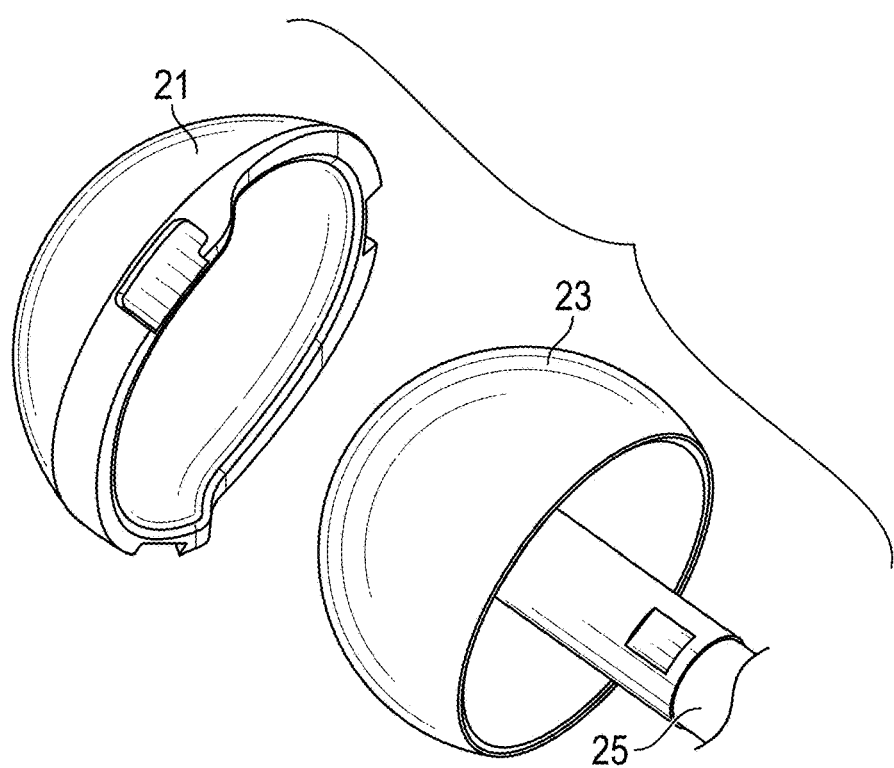
FIG. 5 is an exploded perspective view of an acetabular cup and a femoral head portion of an implant.

With reference to FIG. 5, the implant includes an acetabular cup 21 that is configured to be inserted into an acetabulum anatomy of the pelvis. The implant also includes a femoral head 23 and neck rod 25 (a portion of which is seen), wherein according to one possible embodiment the femoral head 23 on a femoral head base may be attached to the femoral neck rod 25 with a tapered end 27. The femoral head 23 is configured to interface with the acetabular cup 21 as a smooth spherical-surface joint. As already mentioned, the acetabular cup 21 is composed of a bio-compatible metal, while the femoral head 23 is composed of a durable bio-compatible polymer, for a smooth spherical metal-plastic joint between the acetabular cup and corresponding femoral head.

Figure 6:
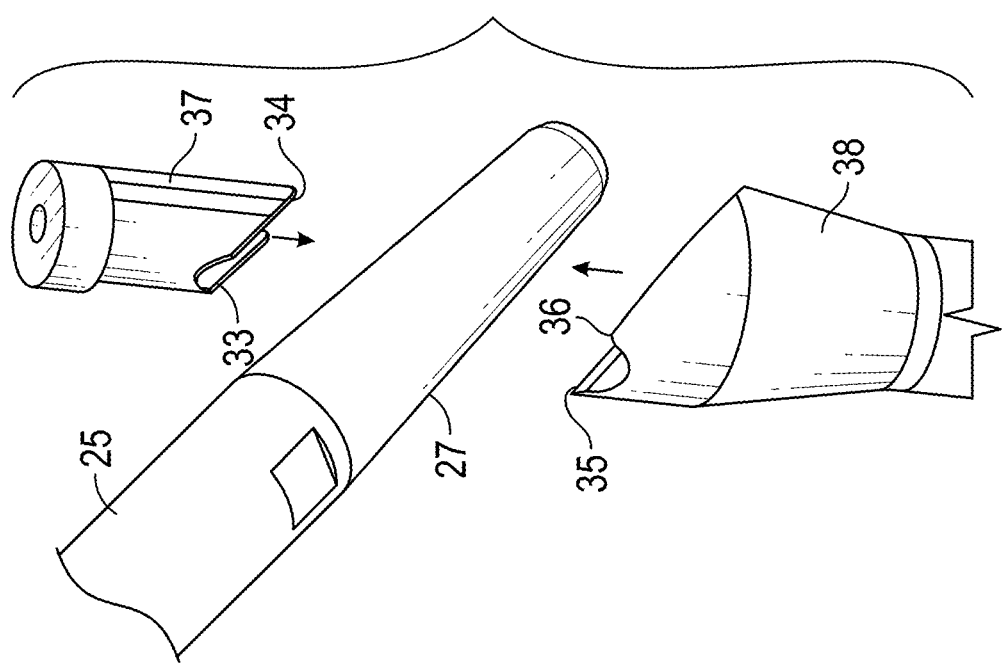
FIG. 6 is a perspective view of the tapered end of an implant neck rod in relation to a main body shaft and compressing connector to illustrate contact surfaces at the taper.

As noted, one key feature of implants in accord with the present invention is that the femoral neck rod 25 has a tapered end 27, as seen in FIG. 6. A main body shaft of the implant is configured to be inserted into a femoral shaft region of the patient's femur and secured by bone screws through cortical bone of the femur. The main body shaft has a diagonal tapered hole 31 therethrough located at the center line of the femoral neck to receive the tapered end 27 of the femoral neck rod 25.

FIG. 6 shows an isometric view of the tapered portion 27 at an end of the implant's neck rod 25 and a stem component 37 of a hip implant. The stem component 37 holds the tapered portion 27 against the implant's main body shaft 38. Contact edge lines 33-36 where the stem 37 and main shaft 38 contact the tapered surface 27 are shown in the view as well. The taper in the neck's end portion 27 is generally in a range of about two to four degrees relative to a non-tapered (cylindrical) shape.

Figure 7:
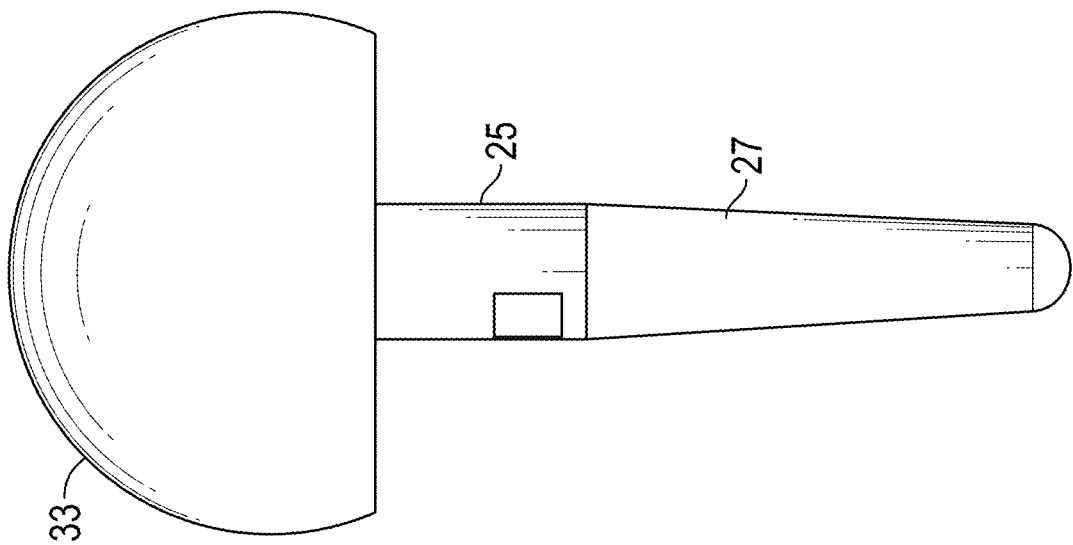
FIG. 7 is a side plan view of femoral head and neck portion of an implant in accord with the present invention.
Figure 8:
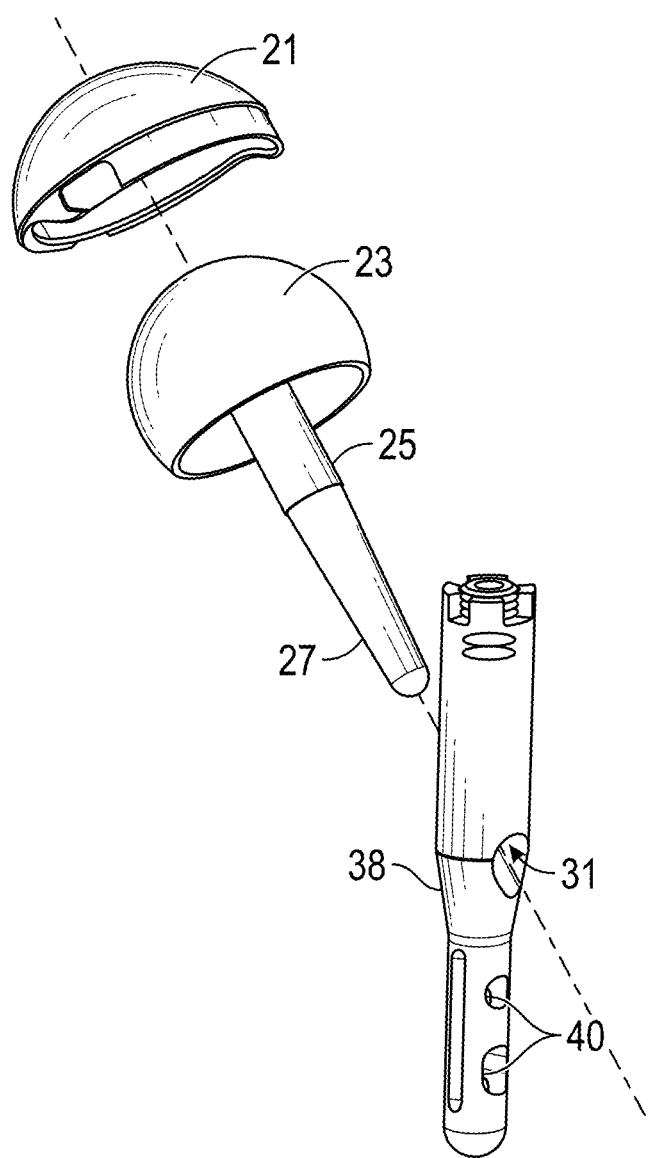
FIGS. 8 and 9 are respective exploded and assembled perspective views of an implant in accord with the present invention showing insertion of the tapered neck rod into an angled hole of an implant stem body.
Figure 9:
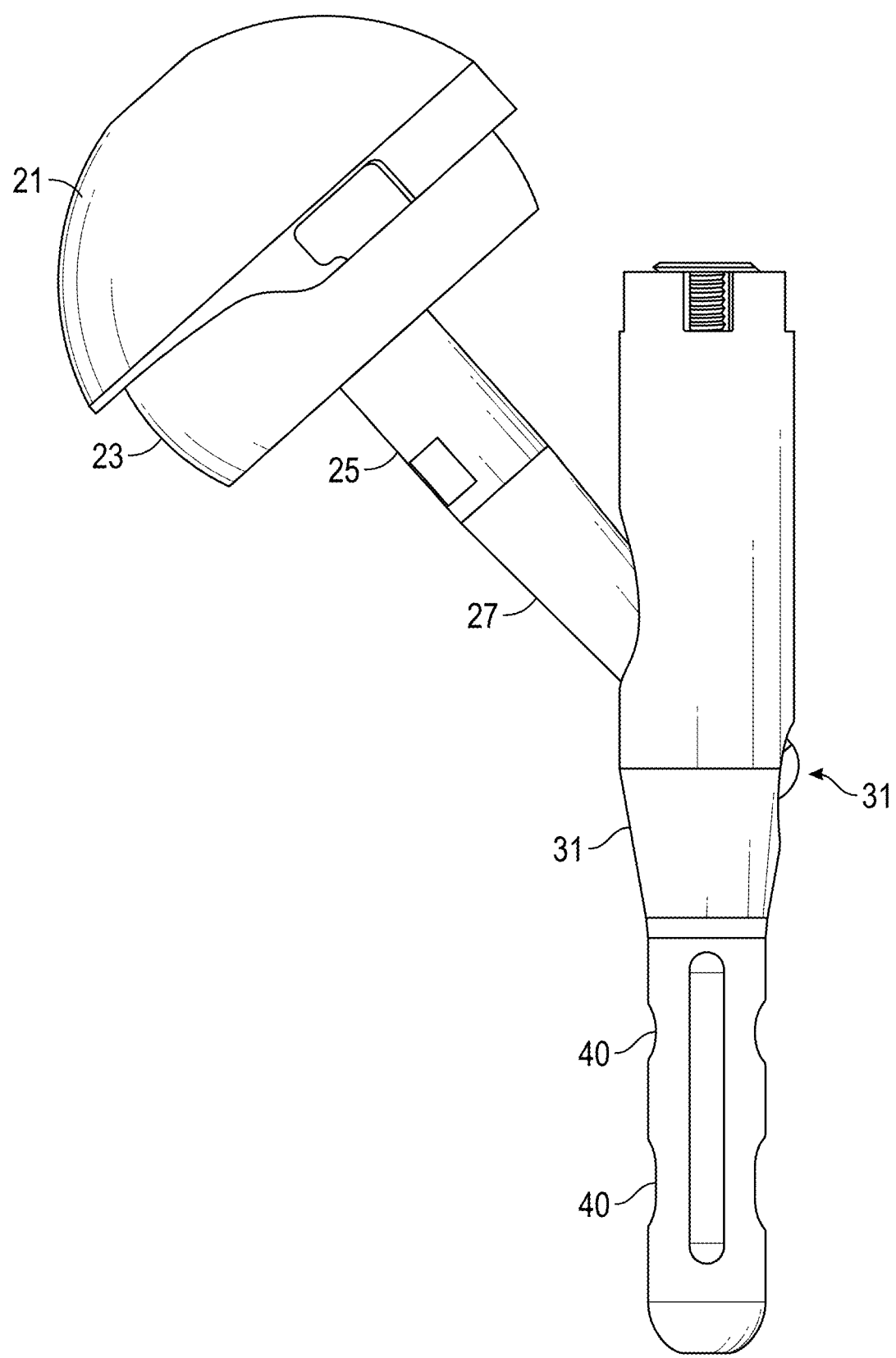

FIGS. 7-9 further illustrate this tapered neck-main body shaft connection. FIG. 7 shows the complete head and neck portion of the implant. The femoral head 23 is connected to the neck rod 25 which terminates in a tapered portion 27, where the degree of taper typically falls in a range from 2° to 4°. As seen in FIGS. 8 and 9, the acetabular cup 21 is slidably seated against the femoral head 23 in a smooth metal-polymer spherical-surface joint. The tapered end portion 27 of the neck rod 25 is inserted through an angled opening in the main shaft 38, which has a substantially matching degree of taper. The main shaft 38 will be firmly seated vertically within the upper femur, attached to the bone by screws through a pair of horizontal openings 40 in the shaft 38.

Figure 10:
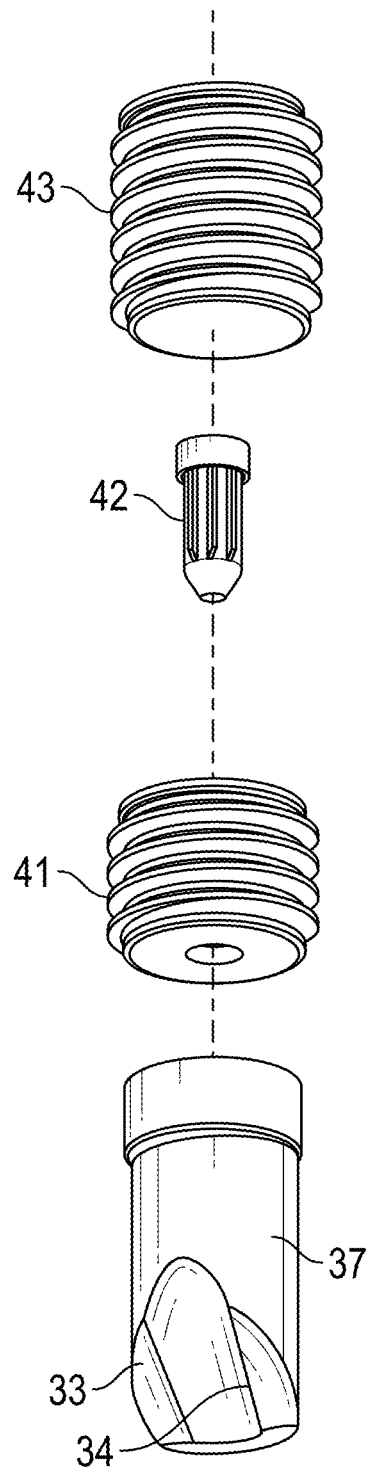
FIG. 10 is a perspective view of a compression screw set and compressor element for insertion into a main body shaft.

As seen in FIGS. 8-10, a screw-down compressing connector 37 is provided, which when inserted into the main shaft 38 will serve to hold the tapered end portion 27 of the neck rod 25 firmly in place within the angled opening 31 via compression along contact lines 33 and 34. A locking screw set 41-43 forms a self-locking joint that holds the compressing connector 37 against the end portion 27 with a specified amount of applied pressure. The pin 42 allows the pressure applied by the bottom screw 41 to be finely adjusted. Top screw 43 forms the jam that keeps the screw 41 from loosening.

In FIGS. 11 and 12, the angled opening 31 in the main shaft 38 is viewed from slightly different perspectives (and without insertion of the tapered end portion 27) to reveal respective upper and lower portions of that opening 31. The upper portion is seen in FIG. 11 to have the contact lines 33 and 34 at the bottom of the compressing connector 37 protruding slightly into the opening 31 from above. The lower portion is seen in FIG. 12 to also have contact lines 35 and 36 formed by the shape of the opening 31.

Figure 13A:
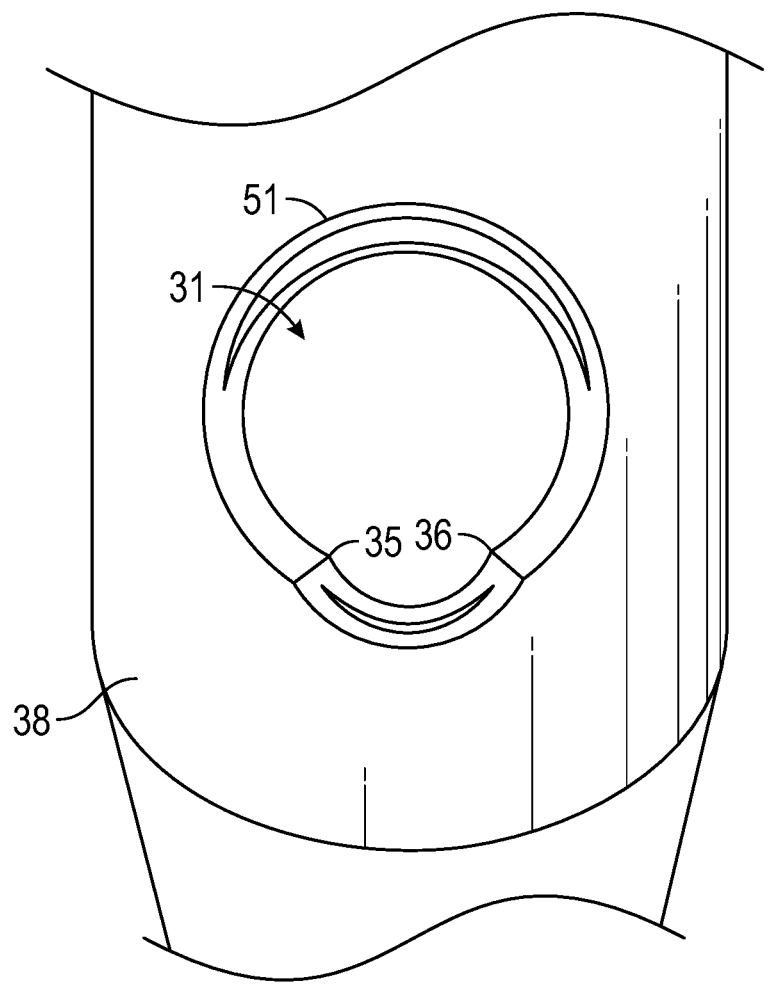
FIGS. 13A and 13B respectively show a close sagittal view and a coronal schematic view of the angled opening in the main stem, showing a hole cross-section according to one embodiment of the present invention.
Figure 13B:
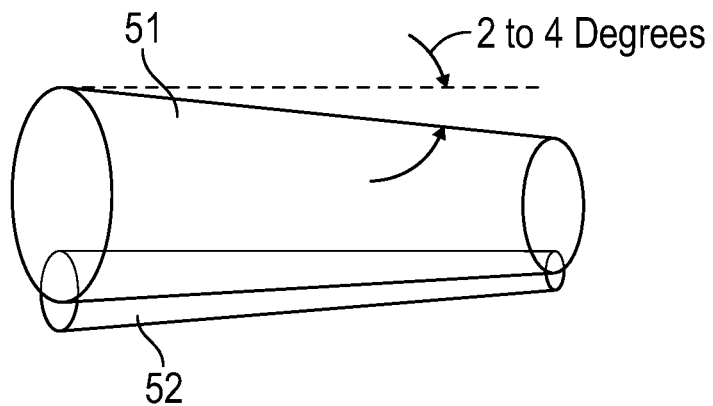

FIGS. 13A and 13B show a close sagittal view and coronal schematic view of the angled opening 31 in the main shaft 38, with particular attention to its cross-sectional shape that allow it to work together when the tapered end of the neck rod is inserted. In a preferred embodiment, there are two overlapping circle shape holes 51 and 52 which can be constructed, both with an interior taper angle ranging anywhere from two to four degrees. As seen, the two circular cross-sections need not necessarily have the same radius, and the degree of overlap can also vary. The corresponding tapered end 27 of the neck will be tapered to the same degree as the respective hole 31. The overlapping circular cross-section of the hole 31 help prevent unwanted axial rotations of the implant's head and neck. Other noncircular hole cross-sections (e.g. elliptical) could also achieve this function.

Figure 14A:
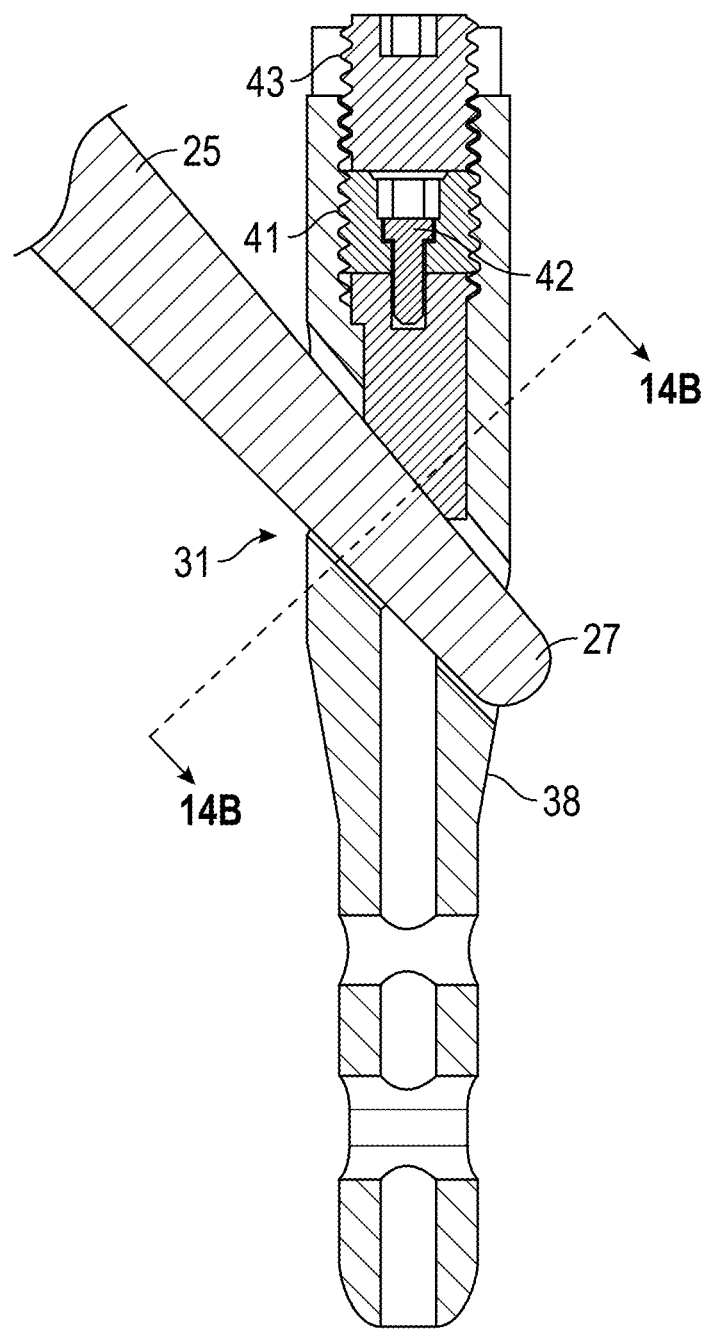
FIGS. 14A, 14B are coronal and sagittal cross-sectional views of the main stem and tapered end of the neck, with the sectioning of FIG. 14B taken along the line A-B in FIG. 14A.
Figure 14B:
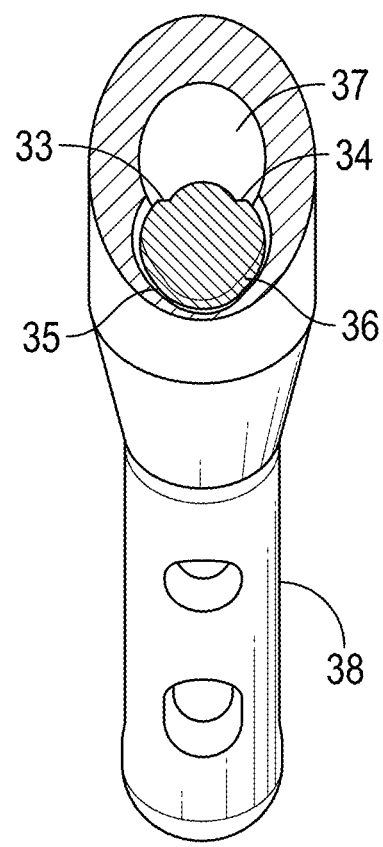

With reference to FIGS. 14A and 14B, the tapered end 27 of the neck rod 25 has two contact edge lines 33 and 34 with the compressing connector piece 37, held down by locking screw set 41-43, and two contact edge lines 35 and 36 with the bottom of the hole 31 in the main body shaft 38. When the tapered end 27 is pushed inside the main body shaft 38, these contact edge lines 33-36 will firmly hold the implant neck from the bending and axial forces and accommodate the implant stability.

Figure 15A:
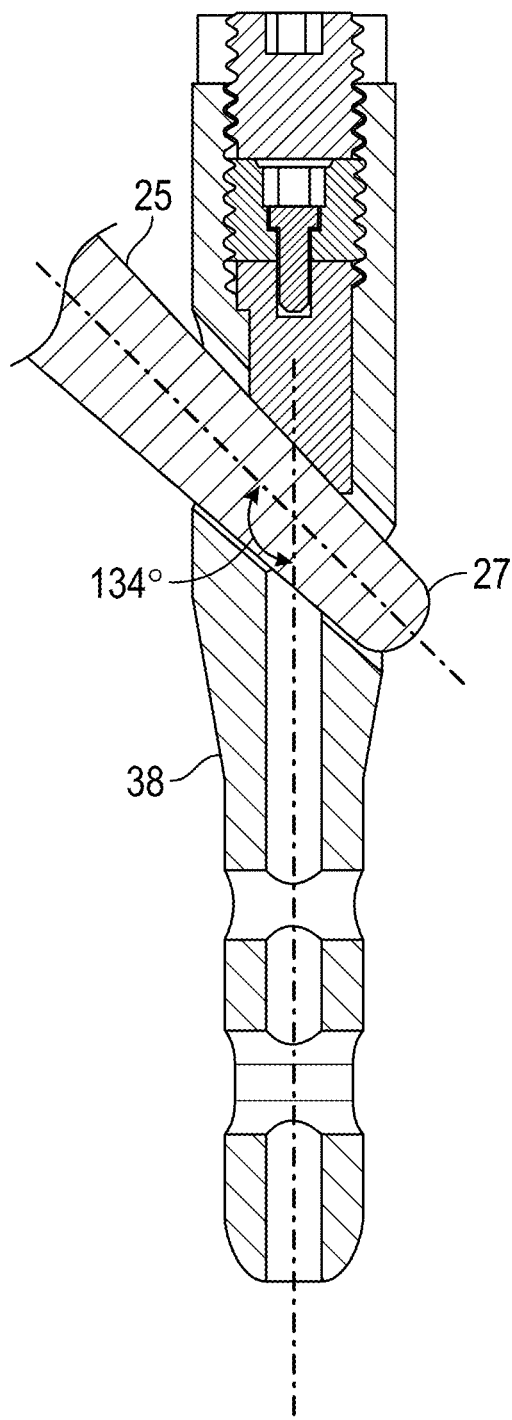
FIGS. 15A and 15B show side sectional views of two implant embodiments having different specific femoral angles.
Figure 15B:
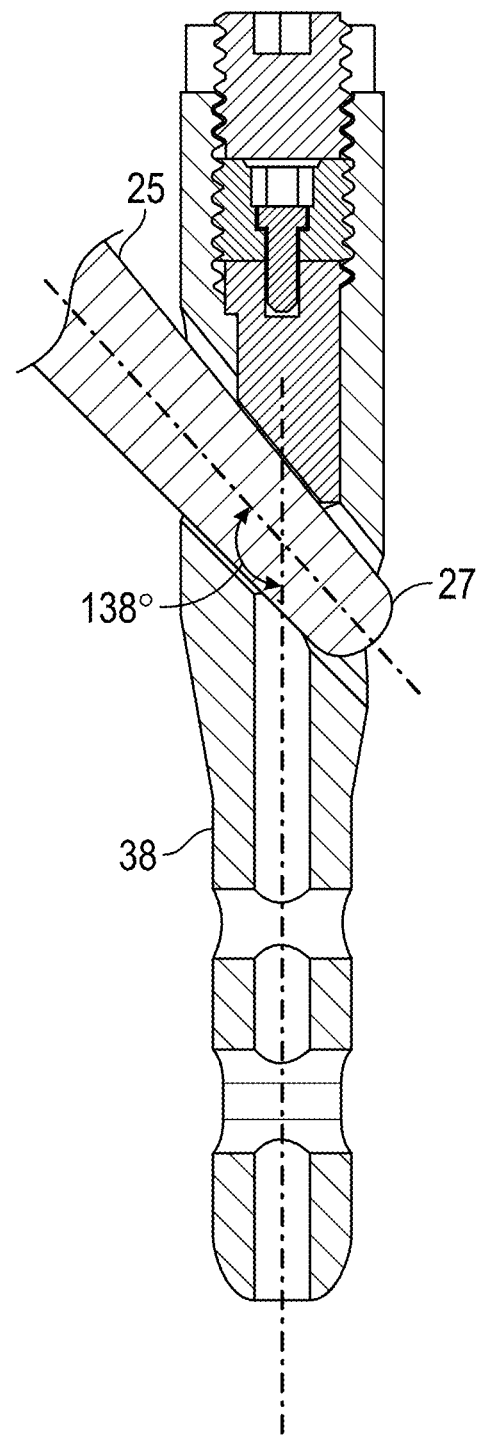

An implant made in accord with the present invention can be used even in patients with a chance of developing or continuing osteonecrosis. The tapered neck 27 of the implant will be fixed inside the main body shaft 38 by compression and prevent the implant from bending and causing an implant failure. There can be two different embodiments, each with its own specific fixed angle (134°±2°, 138°±2°) of the neck rod 25 relative to the main body shaft 38, as shown in FIGS. 15A and 15B. Together, these two designs cover most existing hip anatomies, which generally has a 136°±4° femur angle. The choice of which implant embodiment to use will depend upon the specific patient's femur angle.

Figure 16A:
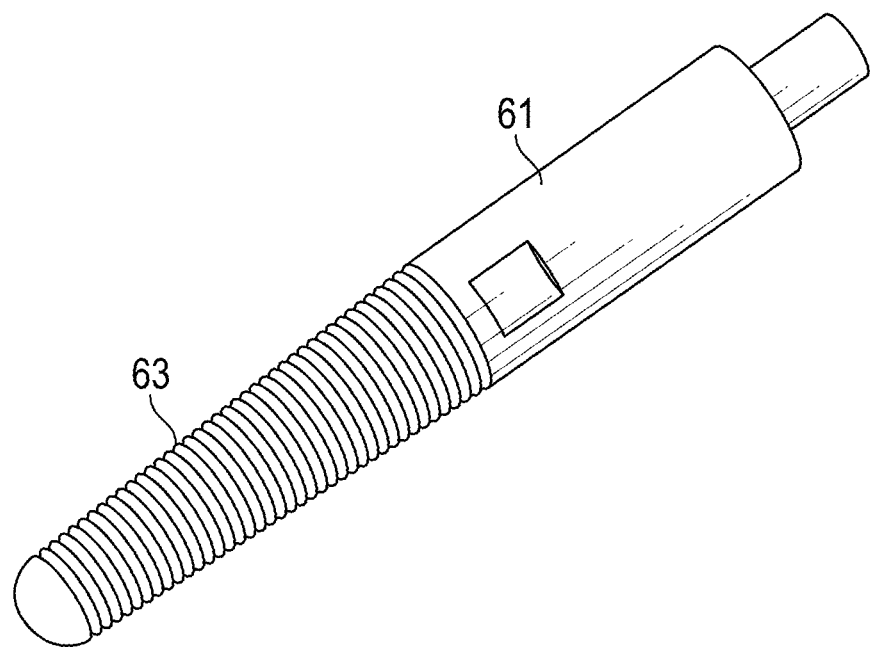
FIGS. 16A and 16B are, respectively, an isometric view and close-up view of an implant neck embodiment that has wedge-shaped locking surfaces.
Figure 16B:
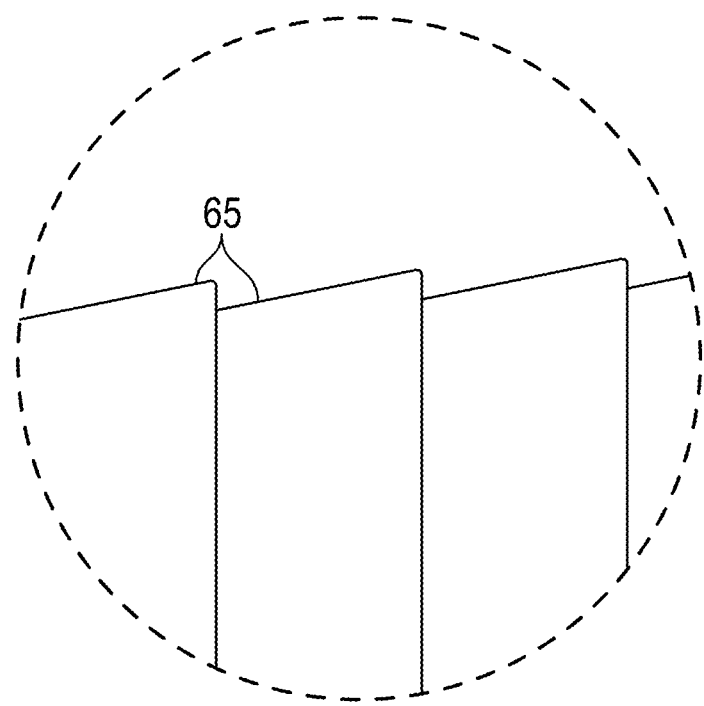

FIGS. 16A and 16B illustrate another option for a tapered neck rod 61 to further increase the stability of the implant. Specifically, the tapered end 63 of the neck rod 61 may have a set of wedge-shaped locking surfaces 65 that can act as a linear ratchet to keep the neck rod 61 from compressively slipping further into the main stem of the implant, despite the tapered hole. The end of the compressing connector in the main stem will engage those locking features 65.

The invention claimed is:

1. A hip implant, comprising:
A metallic acetabular cup configured to be inserted into an acetabulum anatomy of a pelvis;
a femoral head and neck portion with a polymer femoral head on a femoral head base that is attached to a femoral neck rod, the polymer femoral head configured to interface with the metallic acetabular cup as a smooth spherical-surface joint, the femoral neck rod configured to be inserted along a center line into a neck of the femur and having a tapered end with a taper angle in a range from two to four degrees; and
a main body shaft configured to be inserted into a femoral shaft region of femur and secured by bone screws through cortical bone of the femur, the main body shaft having a linear central axis that extends an entire length of the main body shaft, the main body shaft also having a diagonal hole therethrough located at the center line of the neck of the femur so as to receive the tapered end of the femoral neck rod at an angle that aligns with center line of the neck, the diagonal hole having a taper angle in a range from two to four degrees that substantially matches the taper angle of the tapered end of the femoral neck rod, the main body shaft also having a secured lock mechanism insertable therein above the diagonal hole that is screwed down to compressively engage the tapered end of the femoral neck rod within the diagonal hole.

2. The hip implant as in claim 1, wherein the diagonal hole through the main body shaft has a cross-section in the form of two overlapping circles with edge surfaces engaging the tapered end of the femoral neck rod within the angled hole.

3. The hip implant as in claim 1, wherein the diagonal hole through the main body shaft is at a specified femoral angle in a range from 132 to 140 degrees between axes of the main body shaft and femoral neck rod.

4. The hip implant as in claim 1, wherein the tapered end of the femoral neck rod has a locking surface made up of an axially disposed set of circumferential wedges.

5. The hip implant as in claim 1, wherein the acetabular cup, femoral neck rod and main body shaft are composed of a bio-compatible metal comprising any of cobalt, chromium, titanium, alloys thereof and medical-grade stainless steel 316.

6. The hip implant as in claim 1, wherein the femoral head is composed of a bio-compatible polymer comprising any of polyethylene, polyether ether ketone (PEEK), and ultra-high-molecular-weight polyethylene (UHMWPE).

* * * * *